United States Patent [19]

Tuttle

[11] 4,338,101
[45] Jul. 6, 1982

[54] PROCESS AND APPARATUS FOR RECOVERING HYDROCARBONS FROM INERT GAS-HYDROCARBON VAPOR MIXTURES

[75] Inventor: Willard N. Tuttle, Tulsa, Okla.

[73] Assignee: John Zink Company, Tulsa, Okla.

[21] Appl. No.: 289,511

[22] Filed: Aug. 3, 1981

[51] Int. Cl.³ .................... B01D 53/04; B01D 53/14
[52] U.S. Cl. ........................................ 55/48; 55/58;
 55/62; 55/74; 55/88; 55/180; 55/208; 55/387
[58] Field of Search ................. 55/28, 37, 48–51,
 55/55, 58, 62, 68, 74, 88, 89, 179–181, 189, 208,
 222, 387; 220/85 VR, 85 VS

[56] References Cited
U.S. PATENT DOCUMENTS

| | | | |
|---|---|---|---|
| 2,947,379 | 8/1960 | Aubrey | 55/88 |
| 3,225,518 | 12/1965 | Skarstrom et al. | 55/58 X |
| 3,455,089 | 7/1969 | Mattia | 55/62 |
| 3,543,484 | 12/1970 | Davis | 55/387 |
| 3,768,232 | 10/1973 | Farber et al. | 55/58 |
| 3,776,283 | 11/1973 | Kramer et al. | 55/387 X |
| 3,867,111 | 2/1975 | Knowles | 55/58 X |
| 3,897,193 | 7/1975 | Kattan et al. | 55/387 X |
| 3,979,175 | 9/1976 | Kattan et al. | 55/48 |
| 4,056,369 | 11/1977 | Quackenbush | 55/58 |
| 4,066,423 | 1/1978 | McGill et al. | 55/48 |
| 4,104,039 | 8/1978 | Kuri et al. | 55/58 X |
| 4,261,716 | 4/1981 | Schwartz et al. | 55/387 |
| 4,276,058 | 6/1981 | Dinsmore | 55/48 |
| 4,305,734 | 12/1981 | McGill | 55/58 X |

*Primary Examiner*—Robert H. Spitzer
*Attorney, Agent, or Firm*—Laney, Dougherty, Hessin & Beavers

[57] ABSTRACT

A process and apparatus for recovering hydrocarbons from inert gas-hydrocarbon vapor mixtures wherein the mixture is caused to flow through a bed of solid adsorbent whereby the hydrocarbons are removed from the mixture and a residue gas stream comprised of substantially hydrocarbon-free inert gas is produced. A second bed of solid adsorbent having hydrocarbons previously adsorbed thereon is regenerated by evacuating the bed and the inert gas-hydrocarbon vapor mixture produced by the evacuation is contacted with a liquid absorbent whereby a major portion of the hydrocarbons are absorbed therefrom and recovered. The evacuation of the beds is accomplished using a vacuum pump with an integral cooling jacket for cooling the pump as well as the fluids pumped thereby attached thereto. A cooling medium such as the rich liquid absorbent produced in the process is caused to flow through the vacuum pump cooling jacket thereby cooling the pump and the inert gas-hydrocarbon mixture pumped thereby.

21 Claims, 1 Drawing Figure

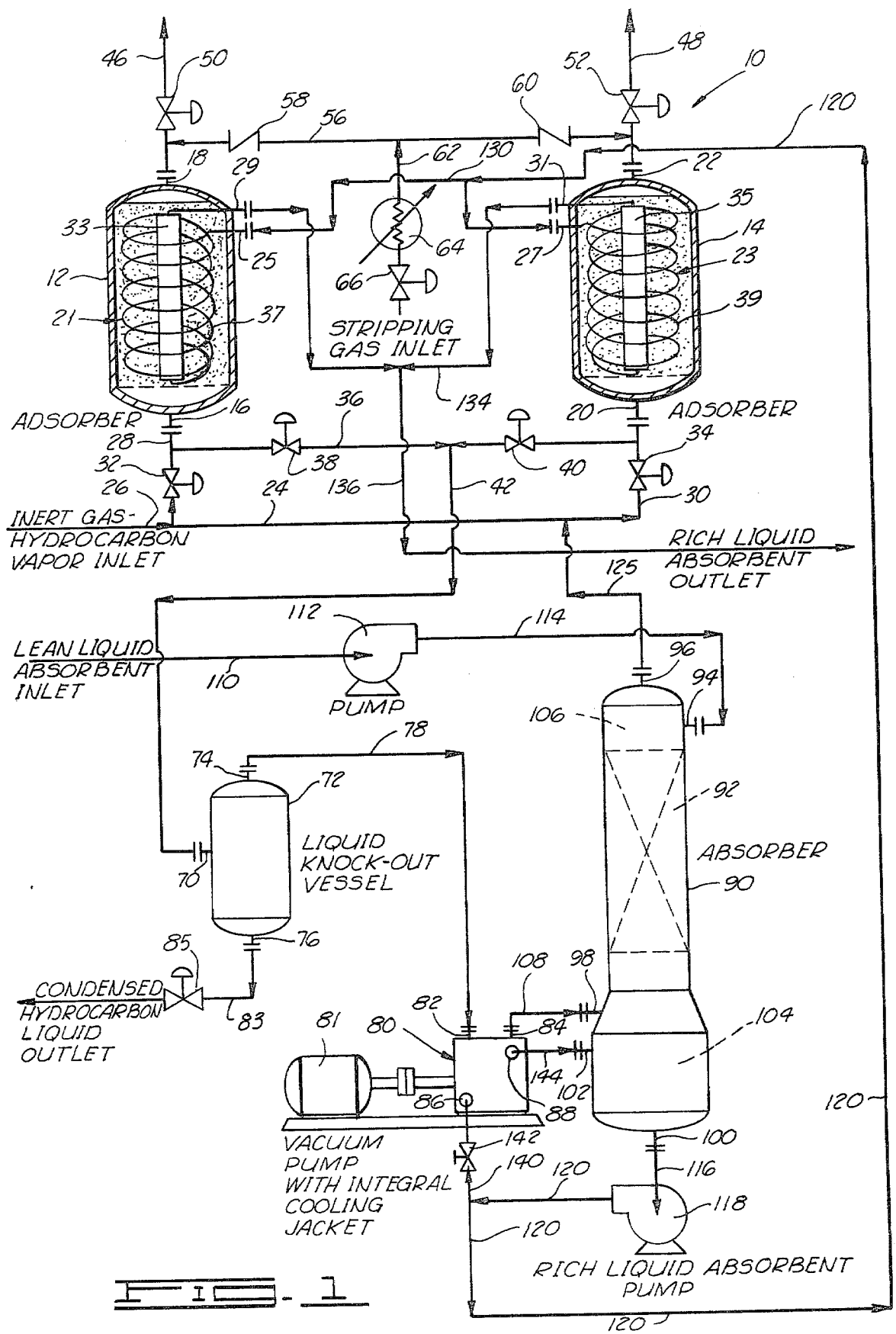

PROCESS AND APPARATUS FOR RECOVERING HYDROCARBONS FROM INERT GAS-HYDROCARBON VAPOR MIXTURES

BACKGROUND OF THE INVENTION

1. Field of the Invention

The present invention relates to a process and apparatus for recovering hydrocarbons from inert gas-hydrocarbon vapor mixtures, and more particularly, but not by way of limitation, to an improved process and apparatus for recovering vaporized gasoline light ends and the like from a mixture thereof with air or other inert gas.

2. Description of the Prior Art

In handling multicomponent hydrocarbon liquids such as gasoline, kerosene, solvents and the like, mixtures of hydrocarbon vapors and inert gases such as air, nitrogen, etc., are often produced which cannot be vented directly to the atmosphere due to the resulting pollution of the environment and the fire and/or explosion hazard. Consequently, a variety of processes and apparatus have been developed and used heretofore for removing hydrocarbon vapors from inert gas-hydrocarbon vapor mixtures whereby the remaining inert gas can be vented to the atmosphere or reused. The removed hydrocarbons are generally liquefied and recombined with the hydrocarbon liquids from which they were vaporized thereby making the recovery economically advantageous.

The term "inert gas" is used herein to mean a gas which does not react with hydrocarbons to a substantial degree and which is not readily adsorbed on beds of solid adsorbent having an affinity for hydrocarbons or readily absorbed in liquid absorbents having an affinity for hydrocarbons. Examples of such inert gases are oxygen, nitrogen, air and the like. For purposes of this disclosure, light hydrocarbon vapors such as methane are considered to be within the definition of "inert gas" when mixed with heavy hydrocarbon vapors such as those utilized in solvents in that while such light hydrocarbons are readily adsorbed on beds of solid adsorbent having an affinity for hydrocarbons they are also readily displaced by the heavier hydrocarbons. In addition, liquid absorbents having an affinity for heavier hydrocarbons can be utilized which do not absorb major portions of lighter hydrocarbons such as methane.

A process for the recovery of light mixed hydrocarbon vapors from an air-hydrocarbon mixture expelled as a result of storage breathing or loading of vented hydrocarbon vessels is described in U.S. Pat. No. 4,066,423 issued Jan. 3, 1978. In accordance with such process, the air-hydrocarbon vapor mixture from which hydrocarbons are to be removed and recovered is passed through a bed of solid adsorbent having an affinity for hydrocarbons. As the mixture passes through the bed, a major portion of the hydrocarbons contained in the mixture are adsorbed on the bed and a residue gas stream is produced which is comprised substantially of hydrocarbon-free air. The hydrocarbon-rich air-hydrocarbon mixture produced as a result of the evacuation regeneration of the bed is contacted with a liquid absorbent whereby hydrocarbons are removed therefrom and the residue gas stream from the absorption step is recycled to the bed through which the inlet air-hydrocarbon mixture is flowing. In accordance with the teachings of U.S. Pat. No. 4,066,423, the liquid absorbent utilized is comprised of liquid hydrocarbons condensed from the air-hydrocarbon vapor mixture produced in the evacuation regeneration step. The use of hydrocarbons which are condensed from the hydrocarbon-rich air-hydrocarbon vapor mixture to contact the remaining air-hydrocarbon vapor mixture results in the inefficient absorption of hydrocarbons from the remaining air-hydrocarbon vapor mixture. In addition U.S. Pat. No. 4,066,423 teaches the use of a liquid ring vacuum pump for evacuating the bed of solid adsorbent being regenerated. The use of such a pump requires elaborate three-phase separation apparatus for separating gases and condensed hydrocarbons from the sealing liquid used as well as apparatus for cooling the sealing liquid which is recirculated to the vacuum pump.

U.S. Pat. No. 4,261,716 issued Apr. 14, 1981, and U.S. Pat. No. 4,276,058 issued June 30, 1981, are directed to processes and apparatus for recovering hydrocarbons from air-hydrocarbon vapor mixtures, and while such processes and apparatus overcomes the problem with inefficient absorption of hydrocarbons from the hydrocarbon-rich air-hydrocarbon vapor mixture mentioned above in connection with U.S. Pat. No. 4,066,423, and are more efficient in removing and recovering hydrocarbons from inlet air-hydrocarbon vapor mixtures, they also disclose that a liquid seal vacuum pump is preferred for use in the apparatus.

Numerous other processes and apparatus for recovering hydrocarbons from air-hydrocarbon vapor mixtures or otherwise treating said mixtures as disclosed in U.S. Pat. Nos. 3,897,193; 3,979,175; 3,867,111; 3,768,232; 3,455,089; 3,543,484; and 3,776,283.

By the present invention, an improved process and apparatus for recovering hydrocarbons from inert gas-hydrocarbon vapor mixtures is provided which overcomes the problem mentioned above, which is more efficient and which is less expensive than the heretofore used process and apparatus.

SUMMARY OF THE INVENTION

A process for recovering hydrocarbons from an inlet inert gas-hydrocarbon vapor mixture comprising the steps of flowing the inlet mixture through a first bed of granular solid adsorbent having an affinity for hydrocarbons whereby hydrocarbons are adsorbed on the bed and a residue gas stream comprised of substantially hydrocarbon-free inert gas is produced which is withdrawn from the bed of granular solid adsorbent. A second bed of granular solid adsorbent having hydrocarbons previously adsorbed thereon is regenerated by evacuation with a vacuum pump having a cooling jacket for cooling the pump and the fluids pumped thereby attached thereto whereby hydrocarbons are desorbed from the bed and a hydrocarbon-rich inert gas-hydrocarbon mixture is produced. Hydrocarbons which condense from the mixture are separated therefrom prior to pumping the mixture with the vacuum pump and a cooling medium is passed through the cooling jacket of the vacuum pump to thereby cool the pump and the inert gas-hydrocarbon mixture pumped thereby. The hydrocarbon-rich inert gas-hydrocarbon mixture pumped by the vacuum pump is contacted with a liquid absorbent whereby a major portion of the hydrocarbons are removed therefrom and a residue gas stream comprised of inert gas and a minor portion of hydrocarbons is produced. The residue gas stream is combined with the inlet inert gas-hydrocarbon mixture and the flow patterns of the inlet inert gas-hydrocarbon mixture and the bed of solid adsorbent being evacuated are periodically changed whereby the bed through which the inlet inert gas-hydrocarbon mixture is flowing becomes loaded with adsorbed hydrocarbons, the inlet inert gas-hydrocarbon mixture is caused to flow through the bed which has just been regenerated. Apparatus for carrying out the process of this invention is also provided.

It is, therefore, a general object of the present invention to provide a process and apparatus for recovering hydrocarbons from inert gas-hydrocarbon vapor mixtures.

A further object of the present invention is the provision of a process and apparatus for recovering hydrocarbons from inert gas-hydrocarbon vapor mixtures wherein the cooling of the vacuum pump and fluids pumped thereby, and optionally, the cooling of the beds of adsorbent is accomplished by passing hydrocarbon-rich liquid absorbent in heat exchange relationship therewith.

Yet a further object of the present invention is the provision of apparatus for recovering hydrocarbons from an inert gas-hydrocarbon vapor mixture which is more economical than apparatus utilized heretofore.

Other and further objects, features, and advantages of the present invention will be readily apparent to those skilled in the art upon a reading of the description of preferred embodiments which follows when taken in conjunction with the accompanying drawing.

BRIEF DESCRIPTION OF THE DRAWING

In the drawing forming a part of this disclosure, apparatus for carrying out the process of this invention is illustrated diagrammatically.

DESCRIPTION OF PREFERRED EMBODIMENTS

Referring now to the drawing, apparatus of the present invention is illustrated and generally designated by the numeral 10. The apparatus 10 is comprised of a pair of adsorbers 12 and 14, each of which contains a bed of granular solid adsorbent through which gases can flow. Each of the adsorbers 12 and 14 are closed vessels and include connections positioned on opposite sides of the beds of adsorbent contained therein. That is, the adsorber 12 includes inlet and outlet connections 16 and 18 and the adsorber 14 includes inlet and outlet connections 20 and 22. While various solid adsorbents having an affinity for hydrocarbons can be utilized in the adsorbers 12 and 14, granular activated carbon is preferred in that it is particularly suitable for adsorbing light hydrocarbon vapors and for vacuum regeneration.

Each of the adsorbers 12 and 14 preferably includes a heat transfer coil 21 and 23, respectively, disposed therein. The heat transfer coils 21 and 23 include inlet connections 25 and 27, respectively, and outlet connections 29 and 31, respectively, which pass through the sides of the closed vessels 12 and 14. The heat transfer coils 21 and 23 are of a configuration and are positioned within the beds of solid adsorbent contained within the adsorbers 12 and 14 such that heat is transferred from the beds of solid adsorbent to a cooling medium flowed through the heat transfer coils. While a great variety of coil configurations can be utilized, a presently preferred configuration includes a central vertically positioned cylinder and a helical coil positioned an intermediate distance outwardly therefrom. More specifically, the heat transfer coils 21 and 23 include centrally positioned cylinders 33 and 35, respectively, the top ends of which are connected to the outlet connections 29 and 31 and the bottom ends of which are connected to vertically positioned helical coils 37 and 39, respectively. The helical coils are in turn connected to the inlet connections 25 and 27, respectively. Thus, cooling medium flows through the heat transfer coils 21 and 23, passes downwardly through the helical coils 37 and 39 thereof and upwardly through the centrally positioned cylinders 33 and 35 thereof.

An inert gas-hydrocarbon vapor mixture inlet header 24 is provided connected to a conduit 26 which conducts an inert gas-hydrocarbon vapor mixture from a source thereof to the apparatus 10. A pair of conduits 28 and 30 are connected to the header 24 and to the connections 16 and 20 of the adsorbers 12 and 14, respectively. Conventional switching valves 32 and 34 are disposed in the conduits 28 and 30, respectively, and a header 36 is connected to the conduits 28 and 30 at points thereon between the switching valves 32 and 34 and the connections 16 and 20 of the adsorbers 12 and 14. A pair of switching valves 38 and 40 are disposed in the header 36 and a conduit 42 is connected to the header 36 at a point between the switching valves 38 and 40.

A pair of residue gas conduits 46 and 48 are provided and are connected to the connections 18 and 22 of the adsorbers 12 and 14. Switching valves 50 and 52 are disposed in the conduits 46 and 48, respectively. Residue gas is withdrawn from the adsorbers 12 and 14 through valves 50 and 52 and conduits 46 and 48. The residue gas can be vented directly to the atmosphere if applicable or the conduits 46 and 48 can conduct the residue gas to a point of storage or reuse.

A stripping gas header 56 is provided connected to the conduits 46 and 48 at locations thereon between the switching valves 50 and 52 and the connections 18 and 22 of the adsorbers 12 and 14. A pair of check valves 58 and 60 are disposed in the header 56 and a conduit 62 is connected to the header 56 at a point between the valves 58 and 60. A heater 64 which can take various forms and a switching valve 66 are disposed in the conduit 62. If the inert gas in the inlet mixture is air, the end of the conduit upstream from the switching valve 66 and the heater 64 is left open to the atmosphere so that air from the atmosphere is drawn into the conduit 62 and a conventional air filter and flame arrestor (not shown) can be attached thereto for preventing solid impurities from entering the absorbers 12 and 14, etc. When the inert gas in the inlet inert gas-hydrocarbon vapor mixture is a gas other than air, the conduit 62 is connected to a source of such inert gas which is free of hydrocarbon vapors.

The conduit 42 connected to the header 36 is connected to the inlet connection 70 of a liquid knockout vessel or separator 72. The separator 72 includes a gas outlet connection 74 and a liquid outlet connection 76. As will be understood, the separator 72 functions to separate any liquid such as condensed hydrocarbons from gases flowing to the separator 72. The gases, namely a mixture of inert gas and hydrocarbon vapors, are withdrawn from the separator 72 by a conduit 78 connected to the gas outlet connection 74 thereof. Separated liquids, i.e., condensed hydrocarbon liquids, are withdrawn from the separator 72 by a conduit 83 connected to the liquid outlet connection 76 thereof. The conduit 83 leads the withdrawn liquids to storage or a point of further processing. A control valve 85 is disposed in the conduit 83 which is operably connected to a control system (not shown) for maintaining a constant level of liquid in the bottom portion of the separator 72.

The inert gas-hydrocarbon vapor mixture flowing through the conduit 78 is conducted to the suction connection 82 of a vacuum pump 80. In accordance with this invention, the vacuum pump 80 is a vacuum pump having a cooling jacket for simultaneously cooling the pump and the gases pumped thereby attached thereto. The vacuum pump includes a suction connection 82 and a discharge connection 84, and the cooling jacket attached thereto includes a cooling medium inlet connection 86 and a cooling medium outlet connection 88. By circulating a cooling medium through the cooling jacket of the vacuum pump 80, i.e., into the cooling jacket by way of the inlet connection 86 and from the cooling jacket by way of the outlet connection 88 thereof, the pump is cooled as are the gases, i.e., inert gas and hydrocarbon vapors, pumped thereby. In the drawing, the pump 80 is illustrated driven by an electric motor 81, but other drive means can be used. Examples of vacuum pumps having integral cooling jackets for cooling the pumps and fluids pumped thereby suitable for use in accordance with this invention are the vacuum pumps designated by the tradenames Monovac or Huckepack, Series 002, both manufactured by Busch Incorporated of Virginia Beach, Va.

An absorber 90 is provided for intimately contacting gases passing upwardly therethrough with a liquid absorbent flowing downwardly therethrough. More specifically, the absorber 90 includes conventional vapor-liquid contact trays or packing material 92 for bringing about intimate contact between upwardly flowing gases and downwardly flowing liquid absorbent. The absorber 90 includes a lean liquid absorbent inlet connection 94, a residue gas outlet connection 96, a hydrocarbon-rich inert gas hydrocarbon vapor mixture inlet 98, a hydrocarbon-rich liquid absorbent outlet connection 100 and a hydrocarbon-rich liquid absorbent inlet connection 102. The absorber 90 can take various forms but generally includes an accumulator portion 104 below the trays or packing material 92 and a separation portion 106 above the trays or packing material 92.

The inert gas-hydrocarbon vapor mixture pumped by the vacuum pump 80 is conducted by a conduit 108 to the absorber 90. That is, the conduit 108 is connected between the discharge connection 84 of the vacuum pump 80 and the inlet connection 98 of the absorber 90. A stream of lean liquid absorbent is conducted from a source thereof by a conduit 110 connected thereto and connected to the suction of a lean liquid absorbent pump 112. The discharge of the pump 112 is connected to a conduit 114 which leads a stream of lean liquid absorbent pumped by the pump 112 to the absorber 90, i.e., the conduit 114 is connected to the lean liquid absorbent inlet connection 94 of the absorber 90. Rich liquid absorbent accumulating in the bottom portion 104 of the absorber 90 is withdrawn therefrom by way of a conduit 116 connected to the rich liquid absorbent outlet connection 100 thereof. The conduit 116 is connected to the suction of a rich liquid absorbent pump 118 and the discharge of the pump 118 is connected to a conduit 120. The conduit 120 leads a stream of rich liquid absorbent pumped by the pump 118 and withdrawn from the absorber 90 to a storage facility (not shown) or optionally, to a cooling medium inlet header 130 which is in turn connected to the inlet connections 25 and 27 of the heat transfer coils 21 and 23 disposed in the adsorbers 12 and 14. An outlet header 134 is provided connected to the outlet connections 29 and 31 of the heat transfer coils 21 and 23. A conduit 136 is connected to the header 134 for conducting cooling medium from the header 134. In the embodiment shown in the drawing, the cooling medium utilized to cool the beds of adsorbent within the absorbers 12 and 14 is the rich liquid absorbent flowing through the header 130 by way of the conduit 120. The rich liquid absorbent flows through the heat transfer coils 21 and 23 and is withdrawn therefrom by way of the header 134 and the conduit 136 attached thereto. The conduit 136 leads the stream of rich liquid absorbent to a storage facility (not shown).

A conduit 140 having a conventional flow control valve 142 disposed therein is optionally connected to the conduit 120 and to the cooling medium inlet connection 86 of the vacuum pump 80. A conduit 144 is connected to the cooling medium outlet connection 88 of the vacuum pump 80 and to the rich liquid absorbent inlet connection 102 of the absorber 90. Thus, in the embodiment shown in the drawing, a side stream of rich liquid absorbent withdrawn from the absorber 90 by the pump 118 and flowing through the conduit 120 is withdrawn by way of the conduit 140 and flowed through the cooling jacket of the vacuum pump 80 whereby the vacuum pump and gases pumped thereby are cooled. From the pump 80, the side stream of rich liquid absorbent flows by way of the conduit 144 back into the absorber 90.

Thus, the apparatus illustrated in the drawing utilizes a side stream of rich liquid absorbent withdrawn from the absorber 90 to cool the vacuum pump 80 and the fluids pumped thereby. The side stream is continuously recycled through the cooling jacket of the vacuum pump 80 and the absorber 90. In addition, in the embodiment shown in the drawing, the stream of rich liquid absorbent withdrawn from the absorber 90 is utilized to cool the beds of solid adsorbent contained in the absorbers 12 and 14 by flowing the stream through the heat transfer coils 21 and 23 disposed therein. From the heat transfer coils 21 and 23, the stream of rich liquid absorbent is conducted to storage facilities.

As will be understood, cooling media other than rich liquid absorbent can be utilized for cooling either or both the vacuum pump 80 and the beds of adsorbent in the adsorbers 12 and 14 if conditions and economics dictate. In this regard, the vacuum pump 80 can include an integral cooling water and antifreeze system similar to that utilized with an automobile engine whereby cooling water and antifreeze are continuously cooled and recirculated through the cooling jacket of the vacuum pump 80. Various other apparatus and systems can be utilized for causing cooling media to flow through the cooling jacket of the vacuum pump 80 and through the heat transfer coil disposed within the absorbers 12 and 14.

In the embodiment shown in the drawing wherein rich liquid absorbent is utilized as the cooling medium for the heat transfer coils 21 and 23 disposed within the adsorbers 12 and 14, the rich liquid absorbent is continuously flowed through the heat transfer coils whereby the beds of adsorbent contained in the adsorbers 12 and 14 are continuously cooled. However, both in the case where rich liquid absorbent is utilized or a separate cooling medium is utilized to cool the beds of adsorbent, switching valves can be disposed in the headers 130 and 134 and operated in a manner whereby the rich liquid absorbent or other cooling medium is caused to flow through the heat transfer coils 21 and 23 only when the inlet inert gas-hydrocarbon vapor mixture is flowing through the adsorber in which the heat transfer coil is diposed whereby the bed of adsorbent is prevented from overheating. As will be understood by those skilled in the art, the valves 32, 34, 38, 40, 50, 52, 66 and 85 can be operated manually, but are preferably automatically operated valves which are controlled by conventional cycle control instrumentation (not shown). The length of the cycle, i.e., the period of time between when the valves are operated, can be controlled by a timer or other instrument sensing one or more variables in the operation of the apparatus 10, such as the degree of vacuum achieved in the adsorbent bed being regenerated, the composition of the gas stream being vented to the atmosphere, etc.

Operation of the Apparatus 10

In operation of the apparatus 10, the valves 32, 34, 38, 40, 50 and 52 are operated in a manner whereby the inlet inert gas-hydrocarbon vapor mixture is caused to flow through one of the adsorbers 12 or 14 while the other of the adsorbers is being evacuated and regenerated. For example, during a first cycle, the switching valve 32 is open and the switching valve 34 is closed whereby the inlet air-hydrocarbon vapor mixture flows into the adsorber 12 by way of the conduit 28, switching valve 32 and connection 16 of the adsorber 12. Because the switching valve 34 disposed in the conduit 30 is closed, the inlet inert gas-hydrocarbon vapor mixture is prevented from entering the adsorber 14. The switching valve 50 disposed in the conduit 46 is open and the switching valve 52 disposed in the conduit 48 is closed whereby the residue gas stream produced in the adsorber 12 is withdrawn therefrom by way of the connection 18 thereof, the conduit 46 and the switching valve 50 and exits to the atmosphere or other destination. The switching valve 38 disposed in the header 36 is closed and the switching valve 40 disposed therein is open whereby the adsorbent bed within the adsorber 14 is communicated with the conduit 42 by way of the connection 20 of the adsorber 14, the header 36 and the open switching valve 40. The switching valve 66 disposed in the conduit 62 is initially closed.

During the first part of the cycle when the switching valves are in the mode described above, the inlet inert gas-hydrocarbon vapor mixture flows through the bed of adsorbent within the adsorber 12 so that hydrocarbons are adsorbed on the bed and removed from the mixture. The residue gas produced which is comprised of substantially hydrocarbon-free inert gas is withdrawn from the adsorber 12 as described above. Simultaneously, the bed of adsorbent disposed within the adsorber 14 is evacuated by the vacuum pump 80, the suction connection of which is connected to the conduit 42 by way of the liquid knockout vessel or separator 72 and the conduit 78 connected to the gas outlet connection 74 thereof. A hydrocarbon-rich inert gas-hydrocarbon vapor mixture is withdrawn from the adsorbent bed within the adsorber 14 which flows through the conduit 42, the separator 72, the conduit 78 to the vacuum pump 80. As indicated previously, any hydrocarbons which condense are removed from the separator 72 by way of the conduit 83 connected to the liquid outlet connection 76 thereof. The control valve 85 is automatically opened and closed by a conventional level controller or other control means whereby only condensed hydrocarbon liquids are withdrawn from the separator 72 by way of the conduit 80. The inert gas-hydrocarbon mixture withdrawn from the separator 72 by the conduit 78 is pumped by the vacuum pump 80 and discharged therefrom by way of the discharge connection 84 thereof into the absorber 90 by way of the conduit 108 and the inlet connection 98 of the absorber 90. The vacuum pump 80 and the inert gas-hydrocarbon vapor mixture pumped thereby are continuously cooled by a stream of cooling medium which is flowed through the cooling jacket of the vacuum pump 80 by way of the cooling jacket inlet and outlet connections 86 and 88. As shown in the drawing, the cooling medium is rich liquid absorbent withdrawn from the absorber 90.

The inert gas-hydrocarbon vapor mixture entering the absorber 90 by way of the inlet connection 98 thereof flows upwardly through the vapor-liquid contact material 82 wherein it is intimately contacted with lean liquid absorbent flowing downwardly therein, i.e., lean liquid absorbent conducted from a source thereof into the inlet connection 94 of the absorber 90 by way of the conduit 110, the lean liquid absorbent pump 112 and the conduit 114. As the inert gas-hydrocarbon vapor mixture is contacted by the liquid absorbent which flows downwardly within the absorber 90, hydrocarbons are absorbed by the liquid absorbent and removed from the vapor mixture so that a residue gas stream comprised of inert gas and a minor portion of hydrocarbons is produced. The residue gas stream exits the absorber 90 by way of the outlet connection 96 thereof and the conduit 125 and flows into the header 24 where it combines with the inlet inert gas-hydrocarbon vapor mixture and flows through the adsorber 12. As will be understood, the hydrocarbons contained in the residue gas stream are readsorbed on the bed of adsorbent within the adsorber 12 along with hydrocarbons from the inlet inert gas-hydrocarbon vapor mixture. The hydrocarbon-rich liquid absorbent accumulating in the accumulator portion 104 of the absorber 90 is withdrawn therefrom by way of the rich liquid absorbent outlet connection 100, the conduit 116, the pump 118 and the conduit 120. If the rich liquid absorbent is not utilized as cooling medium for the vacuum pump 80 and/or the heat transfer coils disposed in the adsorbers 12 and 14, the conduit 120 leads the rich liquid absorbent to storage facilities (not shown).

During a latter part of the cycle and after a major portion of hydrocarbons adsorbed on the bed of adsorbent within the adsorber 14 have been desorbed therefrom by the operation of the vacuum pump 80, the switching valve 66 in the conduit 62 is opened whereby a relatively small quantity of hydrocarbon-free inert gas enters the conduit 62, flows through the optional heater 64 so that it is heated and then flows by way of the header 56, the check valve 60 and the connection 22 of the adsorber 14 into the absorber 14. The hydrocarbon-free gas flows through the adsorbent contained in the adsorber 14 and is withdrawn therefrom by the vacuum pump 80 as previously described. The introduction of a quantity of hydrocarbon-free gas into the adsorbent bed contained within the adsorber 14 functions to strip additional hydrocarbons from the bed which were not desorbed therefrom by vacuum pumping. Although the apparatus shown in the drawing includes the heater 64, this element is optional in that the same stripping efficiency can be accomplished without heating by increasing the quantity of inert gas introduced into the apparatus 10. The combination of initially evacuating the adsorber 14 by vacuum pumping and stripping the adsorbent bed with hydrocarbon-free inert gas brings about the regeneration of the bed.

After the adsorbent bed within the adsorber 14 has been fully regenerated and the adsorbent bed within the adsorber 12 loaded with hydrocarbons from the inert gas-hydrocarbon vapor mixture flowing therethrough, the switching valve 66 is closed, the switching valves 32 and 50 are closed, the switching valves 34 and 52 are opened, the switching valve 38 is opened and the switching valve 40 is closed. This causes the flow pattern of the inlet inert gas-hydrocarbon vapor mixture to be changed so that the mixture flows through the regenerated adsorbent bed within the adsorber 14 and the residue gas therefrom withdrawn. The adsorbent bed within the adsorber 12 is simultaneously communicated with the vacuum pump 80 whereby it is evacuated and the switching valve 66 is opened during a latter part of the cycle as described above to strip the adsorbent bed within the adsorber 12 so that additional hydrocarbons are desorbed therefrom.

As will be understood by those skilled in the art, the flow pattern of the inlet air-hydrocarbon vapor mixture and the bed being regenerated are continuously changed or recycled so that when the adsorbent bed through which the inlet vapor mixture is flowing becomes loaded with adsorbed hydrocarbons, the inlet mixture is caused to flow into the bed which has just been regenerated. The hydrocarbon-rich inert gas-hydrocarbon mixture produced from the bed being regenerated is continuously contacted with liquid absorbent in the absorber 90 so that the hydrocarbons are recovered.

In the embodiment shown in the drawing, the rich liquid absorbent pumped from the absorber 90 by the pump 118 is conducted by the conduit 120 to the cooling medium inlet header 130. From the header 130, equal portions of the rich liquid absorbent are caused to flow through the heat transfer coils 21 and 23 disposed in the beds of solid adsorbent within the adsorbers 12 and 14 thereby cooling the beds of adsorbent and preventing the overheating thereof due to exothermic reactions taking place therein and/or therewith. The rich liquid absorbent exits the transfer coils 21 and 23 by way of the cooling medium outlet header 134 and is withdrawn therefrom by the conduit 136 which conducts the mixture to storage facilities. As mentioned above, the conduit 120 can lead the rich liquid absorbent directly to storage facilities and a separate cooling medium such as cooling water, another cool process stream, etc., can be conducted to the heat transfer coils 21 and 23 by way of the cooling medium inlet header 130. In some applications the cooling of the adsorbent beds within the adsorbers 12 and 14 can be omitted completely, and in such applications, the heat transfer coils 21 and 23 and the various headers and conduits connected thereto are omitted from the apparatus 10.

In the embodiment shown in the drawing, a portion of the rich liquid absorbent pumped by the pump 118 is continuously withdrawn from the conduit 120 by the conduit 140 and caused to flow through the cooling jacket of the vacuum pump 80 by way of the cooling medium inlet connection 86 and cooling medium outlet connection 88 thereof. The conduit 144 leads the side stream of rich liquid absorbent to the bottom portion 104 of the absorber 90. Thus, a continuous side stream of rich liquid absorbent is recycled through the cooling jacket of the vacuum pump 80, cooling the vacuum pump and the gases pumped thereby. The flow control valve 142 is utilized to regulate the flow rate of the side stream of rich liquid absorbent circulated through the vacuum pump 80. As indicated above, a separate cooling medium such as cooling water or and other cool process stream, can be utilized to cool the vacuum pump 80, and in this case, the conduit 120 leads the rich liquid absorbent from the absorber 90 directly to storage facilities or to the heat transfer coils 21 and 23 in the absorbers 12 and 14.

The apparatus 10 is particularly suitable for recovering vaporized gasoline light ends mixed with air produced as a result of loading gasoline into tank trucks and other vessels. In this application, the air-gasoline vapor mixture is processed in the apparatus 10 as described above and the liquid absorbent utilized is gasoline. That is, stored gasoline is pumped from a storage facility into the absorber 90 and the rich gasoline produced by the apparatus 10 is returned to the gasoline storage facility. Because the stored gasoline is continuously being loaded out of the storage facility and replaced by newly produced gasoline, the stream of gasoline pumped to the absorber efficiently absorbs gasoline light ends. Preferably, the lean gasoline is withdrawn from a separate storage tank from that to which the rich liquid absorbent is conducted to insure the efficient absorption of the vaporized hydrocarbon light ends in the absorber 90.

In order to more clearly illustrate the operation of the apparatus 10, the following example is given.

EXAMPLE

A typical gasoline truck loading terminal has the following loading pattern:

Maximum Instantaneous Rate: 2200 gallons/minute
Maximum throughput in 15 minutes: 16,500 gallons
Maximum throughput in 1 hour: 48,000 gallons
Maximum throughput in 4 hours: 168,000 gallons
Maximum throughput daily: 960,000 gallons The gasoline loaded is deemed to have the following properties:

Summer: 10 psia RVP, 75° F. maximum
Winter: 14 psia RVP, 10° F. minimum

It is recognized that the hydrocarbon concentration of the air-hydrocarbon vapor generated by loading gasoline into truck transports varies according to gasoline volatility and the degree of air saturation attained. However, based on the above gasoline properties and other experience factors known to those skilled in the art, a design hydrocarbon concentration of 35 Vol.% is utilized. The apparatus 10 is designed for an approximate 15 minute cycle time and, consequently, it is necessary for each adsorber 12 and 14 to handle a net air-hydrocarbon vapor influent from the truck loading rack of 353 cubic feet/minute and 2,647 cubic feet each cycle based on a 1.2 vapor growth factor.

Approximately 9,000 pounds of activated carbon is distributed equally in two 7 feet in diameter by approximately 8 feet high adsorbers 12 and 14. Each of the adsorbers 12 and 14 includes a heat transfer coil 21 and 23 for cooling the activated carbon having 110 square feet of outside surface area. A Busch Huckepack Model 437-002 vacuum pump 80 having a cooling jacket attached thereto with a 20 hp electric motor is provided for regeneration of the beds of carbon after each adsorption cycle. Very effective regeneration of the carbon beds is accomplished each cycle by the introduction, under high vacuum conditions, of 30 standard cubic feet of air. The vacuum pump 80 allows attainment of 49 mm of mercury absolute pressure each cycle.

Concentrated hydrocarbon vapors containing 5–20 Vol.% air are discharged from the vacuum pump 80 and conducted to a 2 feet in diameter by approximately 12 feet high absorber 90. A major portion of the hydrocarbon vapors are absorbed and thereby recovered. The residue gas stream containing a minor portion of hydrocarbon vapor exit the top of the absorber 90 by way of the conduit 125 and flow to the adsorber 12 or 14 which is in the adsorption mode.

The pump 112 with a 3 hp electric motor circulates 45 gallons/minute of gasoline from storage facilities to the absorber 90. About 47 gallons/minute of rich gasoline are withdrawn from the absorber 90 and pumped by the pump 118 equipped with a 3 hp motor through the conduit 120 and through the heat transfer coils 21 and 23 disposed in the adsorbers 12 and 14 thereby maintaining the beds of activated carbon therein to temperatures below about 175° F. and preventing the runaway overheating thereof. A side stream of rich liquid absorbent of 5 gallons/minute is circulated by way of the conduit 140, the control valve 142 and the conduit 144 between the cooling jacket of the vacuum pump 80 and the absorber 90, thereby continuously cooling the vacuum pump 80 and the air-gasoline vapor mixture being pumped thereby to a temperature below about 135° F.

The apparatus 10 removes and recovers the hydrocarbon vapors generated from the transport loading rack such that less than 10 milligrams of hydrocarbons are vented to the atmosphere per liter of gasoline loaded. Thus, the present invention is well adapted to carry out the objects and attain the ends and advantages mentioned as well as those inherent therein. While presently preferred embodiments of the invention have been described for purposes of this disclosure, numerous changes in the arrangement of process steps and apparatus elements will suggest themselves to those skilled in the art, which changes are encompassed within the spirit of this invention as defined by the appended claims.

What is claimed is:

1. A process for recovering hydrocarbons from an inlet inert gas-hydrocarbon vapor mixture comprising the steps of:
   (a) flowing said inlet mixture through a first bed of solid absorbent having an affinity for hydrocarbons whereby hydrocarbons are adsorbed on said bed and a residue gas stream comprised of substantially hydrocarbon-free inert gas is produced;
   (b) removing said substantially hydrocarbon-free inert gas from said bed of adsorbent;
   (c) evacuating a second bed of solid adsorbent having hydrocarbons and inert gas adsorbed thereon by vacuum pumping with a vacuum pump having a cooling jacket for cooling said pump and fluids pumped thereby attached thereto whereby a major portion of said hydrocarbons are desorbed from said bed and a hydrocarbon-rich inert gas-hydrocarbon mixture is produced;
   (d) separating hydrocarbons which condense from said inert gas-hydrocarbon mixture from said mixture prior to pumping said mixture with said vacuum pump;
   (e) passing a cooling medium through said cooling jacket of said vacuum pump to thereby cool said pump and said inert gas-hydrocarbon mixture pumped thereby;
   (f) contacting the inert gas-hydrocarbon mixture produced in step (c) and pumped by said vacuum pump in an absorber with a lean liquid absorbent having an affinity for hydrocarbons whereby a major portion of the hydrocarbons are removed therefrom thereby producing a hydrocarbon-rich liquid absorbent stream and a residue gas stream comprised of inert gas and a minor portion of hydrocarbons;
   (g) combining said residue gas stream produced in step (f) with said inlet inert gas-hydrocarbon mixture of step (a) whereby hydrocarbons contained therein are adsorbed on said first bed of solid adsorbent; and
   (h) periodically changing the flow patterns of said inlet inert gas-hydrocarbon mixture and changing the bed of solid adsorbent being evacuated whereby when the beds through which the inlet inert gas-hydrocarbon mixture is flowing becomes loaded with adsorbed hydrocarbons, the inlet inert gas-hydrocarbon mixture is caused to flow through the bed which has just been regenerated.

2. The process of claim 1 which is further characterized to include the step of cooling said beds of solid adsorbent by flowing a cooling medium through heat transfer coils disposed in said beds of solid adsorbent to thereby prevent said beds from over-heating.

3. The process of claim 2 wherein the cooling of said beds of solid adsorbent is carried out at least while said inert gas-hydrocarbon vapor mixture is flowing therethrough.

4. The process of claim 1 which is further characterized to include the step of introducing a quantity of hydrocarbon-free inert gas into said second bed while evacuating said bed whereby additional hydrocarbons are stripped from said bed and additional inert gas-hydrocarbon mixture produced.

5. The process of claim 1 wherein said inert gas is air.

6. The process of claim 5 wherein said hydrocarbons contained in said inlet air-hydrocarbon mixture are vaporized gasoline light ends and the liquid absorbent utilized is gasoline.

7. The process of claim 6 wherein said first and second beds of solid adsorbent are beds of granular activated carbon.

8. The process of claim 4 wherein said hydrocarbon-free inert gas is heated prior to introducing it into said beds.

9. A process for recovering hydrocarbons from an inlet air-hydrocarbon vapor mixture comprising the steps of:
   (a) flowing said inlet mixture through a first bed of activated carbon whereby said hydrocarbons in said mixture are adsorbed on said bed and a residue gas stream comprisesd of substantially hydrocarbon-free air is produced;
   (b) venting said substantially hydrocarbon-free air to the atmosphere;
   (c) evacuating a second bed of activated carbon having hydrocarbons adsorbed thereon with a vacuum pump having a cooling jacket for cooling said pump and fluids pumped thereby attached thereto whereby a major portion of said hydrocarbons are desorbed from said bed and a hydrocarbon-rich air-hydrocarbon vapor mixture is produced;

(d) separating hydrocarbons which condense from said air-hydrocarbon mixture from said mixture prior to pumping said mixture with said vacuum pump;

(e) introducing a quantity of hydrocarbon-free air into said second bed while continuing to evacuate said bed whereby additional hydrocarbons are stripped from said bed and additional air-hydrocarbon vapor mixture is produced;

(f) contacting the air-hydrocarbon mixture produced in steps (c) and (e) and pumped by said vacuum pump in an absorber with a lean liquid absorbent having an affinity for hydrocarbons whereby a major portion of the hydrocarbons are removed therefrom;

(h) passing at least a portion of said hydrocarbon-rich liquid absorbent stream produced in step (f) through said cooling jacket of said vacuum pump to thereby cool said pump and said air-hydrocarbon mixture pumped thereby; and (i) periodically changing the flow pattern of said inlet air-hydrocarbon mixture and changing the bed of activated carbon being evacuated and stripped whereby when the bed through which the inlet air-hydrocarbon mixture is flowing becomes loaded with adsorbed hydrocarbons, the inlet air-hydrocarbon mixture is caused to flow through the bed which has just been evacuated and stripped.

10. The process of claim 9 which is further characterized to include the step of cooling said beds of solid activated carbon by flowing a cooling medium through heat transfer coils disposed therein.

11. The process of claim 10 wherein said beds of activated carbon are cooled at least while said inlet air-hydrocarbon vapor mixture is flowing therethrough to thereby prevent said beds from overheating.

12. The process of claim 11 wherein said cooling medium for cooling said beds of solid activated carbon is said stream of hydrocarbon-rich liquid absorbent produced in step (f).

13. The process of claim 9 wherein the hydrocarbons contained in said inlet air-hydrocarbon mixture are vaporized gasoline light ends and the lean liquid absorbent utilized in step (f) is gasoline.

14. The process of claim 9 wherein the hydrocarbon-free air utilized in step (e) is heated prior to introducing it into said bed.

15. The process of claim 13 wherein the source of lean gasoline utilized in step (f) is a gasoline storage facility and said hydrocarbon-rich produced is conducted to a gasoline storage facility.

16. Apparatus for recovering hydrocarbons from an inert gas-hydrocarbon vapor mixture comprising:

(a) a pair of adsorbers containing beds of solid adsorbent having an affinity for hydrocarbons and having inlet and outlet connections on opposite sides of said beds;

(b) first conduit means connected to the inlet connections of said adsorbers for conducting said inert gas-hydrocarbon vapor mixture to said adsorbers and for evacuating said adsorbers;

(c) valve means disposed in said first conduit means for selectively causing said inert gas-hydrocarbon vapor mixture to flow through one or the other of said adsorbers;

(d) second conduit means connected to the outlet connections of said adsorbers for withdrawing residue gas from said adsorbers;

(e) second valve means disposed in said second conduit means for selectively causing residue gas to be withdrawn from one or the other of said adsorbers;

(f) a vacuum pump having a suction connection and a discharge connection and having a cooling jacket for cooling said pump and the fluids pumped thereby attached thereto, said cooling jacket having a cooling medium inlet connection and a cooling medium outlet connection;

(g) means connected to the cooling medium inlet and cooling medium outlet connections of said vacuum pump heat exchanger for circulating a cooling medium therethrough;

(h) third conduit means connected between the suction connection of said vacuum pump and said first conduit means;

(i) third valve means disposed in said third conduit means for selectively communicating one or the other of said adsorbers with the section connection of said vacuum pump;

(j) liquid knockout means disposed in said third conduit means;

(k) an absorber for contacting an inert gas-hydrocarbon vapor mixture with a liquid absorbent having an inert gas-hydrocarbon vapor mixture inlet connection, a residue gas outlet connection, a lean liquid absorbent inlet connection and a rich liquid absorbent outlet connection;

(l) fourth conduit means connected between the inert gas-hydrocarbon vapor mixture inlet of said absorber and the discharge connection of said vacuum pump; and (m) fifth conduit means connected between the residue gas outlet connection of said absorber and said first conduit means.

17. The apparatus of claim 16 wherein said means for circulating a cooling medium through said vacuum pump cooling jacket comprises:

sixth conduit means connected between said rich liquid absorbent outlet connection of said absorber and storage facilities therefor;

a rich liquid absorbent pump disposed in said sixth conduit means;

seventh conduit means connected between said sixth conduit means downstream of said pump and said cooling medium inlet connection of said vacuum pump cooling jacket;

said absorber including a rich liquid absorbent inlet connection; and eighth conduit means connected between said cooling medium outlet connection of said vacuum pump cooling jacket and said absorber rich liquid absorbent inlet connection.

18. The apparatus of claim 16 which is further characterized to include:

a pair of heat transfer coils, one disposed in each of said adsorbers for cooling said beds of solid adsorbent therein and having cooling medium inlet and outlet connections; and means connected to the cooling medium inlet and outlet connections of said heat transfer coils for circulating a cooling medium therethrough.

19. The apparatus of claim 18 wherein said means connected to the inlets and outlets of said heat transfer coils for circulating a cooling medium through said coils comprises:
- a cooling medium pump having a suction connection and a discharge connection;
- sixth conduit means connected between the suction connection of said cooling medium pump and a source of cooling medium;
- seventh conduit means connected between the discharge connection of said cooling medium pump and the inlet connections of said heat transfer coils; and
- eighth conduit means connected between the discharge connections of said heat transfer coils and said source of cooling medium.

20. The apparatus of claim 19 wherein said source of cooling medium is rich liquid absorbent, said sixth conduit means is connected between said suction connection of said cooling medium pump and said rich liquid absorbent outlet connection of said absorber and said eighth conduit means is connected between said discharge connections of said heat transfer coils and rich liquid absorbent storage facilities.

21. The apparatus of claim 18 wherein said means connected to the inlet and outlet connections of said vacuum pump heat exchanger and said means connected to the inlet and outlet connections of said heat transfer coils for circulating cooling medium therethrough comprise:
- sixth conduit means connected between said rich liquid absorbent outlet connection of said absorber and said cooling medium inlet connections of said heat transfer coils;
- a rich liquid absorbent pump disposed in said sixth conduit means;
- seventh conduit means connected between said sixth conduit means downstream of said pump and said cooling medium inlet connection of said vacuum pump cooling jacket;
- said absorber including a rich liquid absorbent inlet connection;
- eighth conduit means connected between said cooling medium outlet connection of said vacuum pump heat exchanger and said absorber rich liquid absorbent inlet connection; and
- ninth conduit means connected between said outlet connections of said heat transfer coil and rich liquid absorbent storage facilitites.

* * * * *